(12) United States Patent
Nakazawa et al.

(10) Patent No.: US 9,262,680 B2
(45) Date of Patent: Feb. 16, 2016

(54) POINT-OF-GAZE DETECTION DEVICE, POINT-OF-GAZE DETECTING METHOD, PERSONAL PARAMETER CALCULATING DEVICE, PERSONAL PARAMETER CALCULATING METHOD, PROGRAM, AND COMPUTER-READABLE STORAGE MEDIUM

(71) Applicant: Japan Science and Technology Agency, Kawaguchi-shi, Saitama (JP)

(72) Inventors: Atsushi Nakazawa, Toyonaka (JP); Christian Nitschke, Toyonaka (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 0 days.

(21) Appl. No.: 14/417,877

(22) PCT Filed: Jul. 24, 2013

(86) PCT No.: PCT/JP2013/070061
§ 371 (c)(1),
(2) Date: Jan. 28, 2015

(87) PCT Pub. No.: WO2014/021169
PCT Pub. Date: Feb. 6, 2014

(65) Prior Publication Data
US 2015/0154758 A1 Jun. 4, 2015

(30) Foreign Application Priority Data
Jul. 31, 2012 (JP) ................................. 2012-169223

(51) Int. Cl.
*G06K 9/00* (2006.01)
*A61B 3/113* (2006.01)
(Continued)

(52) U.S. Cl.
CPC ............ *G06K 9/00604* (2013.01); *A61B 3/113* (2013.01); *A61B 3/15* (2013.01);
(Continued)

(58) Field of Classification Search
None
See application file for complete search history.

(56) References Cited

U.S. PATENT DOCUMENTS

| 4,973,149 A | 11/1990 | Hutchinson |
| 6,359,601 B1 * | 3/2002 | Maguire, Jr. ...................... 345/7 |

(Continued)

FOREIGN PATENT DOCUMENTS

| CN | 102043952 A | 5/2011 |
| JP | 2011-172853 A | 9/2011 |
| WO | 2011/117776 A1 | 9/2011 |

OTHER PUBLICATIONS

State Intellectual Property Office of People's Republic of China, First Office Action, issued in Chinese Patent Application No. 201380013967.7, which is a Chinese counterpart of U.S. Appl. No. 14/417,877, issued on Apr. 8, 2015, 9 pages.

(Continued)

*Primary Examiner* — Shervin Nakhjavan

(57) ABSTRACT

A point-of-gaze detection device according to the present invention detects a point-of-gaze of a subject toward a surrounding environment. The device includes: an eyeball image obtaining means configured to obtain an eyeball image of the subject; a reflection point estimating means configured to estimate a first reflection point, at which incoming light in an optical axis direction of an eyeball of the subject is reflected, from the eyeball image; a corrected reflection point calculating means configured to calculate a corrected reflection point as a corrected first reflection point by correcting the first reflection point on the basis of a personal parameter indicative of a difference between a gaze direction of the subject and the optical axis direction of the eyeball; and a point-of-gaze detecting means configured to detect the point-of-gaze on the basis of light at the corrected reflection point and light in the surrounding environment.

12 Claims, 13 Drawing Sheets

(51) Int. Cl.
  *A61B 3/15* (2006.01)
  *G06F 3/01* (2006.01)
  *G06K 9/46* (2006.01)
  *G06T 7/00* (2006.01)

(52) U.S. Cl.
  CPC ............. *G06F 3/013* (2013.01); *G06K 9/0061* (2013.01); *G06K 9/4661* (2013.01); *G06T 7/0046* (2013.01); *G06T 2207/10004* (2013.01); *G06T 2207/10016* (2013.01); *G06T 2207/20076* (2013.01); *G06T 2207/30201* (2013.01)

(56) References Cited

U.S. PATENT DOCUMENTS

| | | | | |
|---|---|---|---|---|
| 6,373,961 | B1* | 4/2002 | Richardson et al. | 382/103 |
| 6,659,611 | B2 | 12/2003 | Amir et al. | |
| 7,015,950 | B1* | 3/2006 | Pryor | 348/207.11 |
| 7,963,652 | B2 | 6/2011 | Vertegaal et al. | |
| 8,025,405 | B2 | 9/2011 | Rehnstrom | |
| 8,317,327 | B2* | 11/2012 | Cleveland et al. | 351/209 |
| 2003/0098954 | A1* | 5/2003 | Amir et al. | 351/210 |
| 2003/0123027 | A1 | 7/2003 | Amir et al. | |
| 2004/0174496 | A1* | 9/2004 | Ji et al. | 351/209 |
| 2004/0196433 | A1* | 10/2004 | Durnell | 351/209 |
| 2004/0238732 | A1* | 12/2004 | State et al. | 250/250 |
| 2006/0077558 | A1* | 4/2006 | Urakawa et al. | 359/630 |
| 2006/0110008 | A1 | 5/2006 | Vertegaal et al. | |
| 2010/0066975 | A1 | 3/2010 | Rehnstrom | |
| 2011/0018862 | A1* | 1/2011 | Epps | 345/419 |
| 2011/0069277 | A1* | 3/2011 | Blixt et al. | 351/210 |
| 2012/0156652 | A1* | 6/2012 | Lane et al. | 434/11 |
| 2012/0230547 | A1* | 9/2012 | Durnell et al. | 382/103 |
| 2012/0294478 | A1* | 11/2012 | Publicover et al. | 382/103 |
| 2013/0147686 | A1* | 6/2013 | Clavin et al. | 345/8 |

OTHER PUBLICATIONS

Atsushi Nakazawa et al., "Gankyu no Hyomen Hansha to Kosoku Active Hikari Toei o Mochiita Hisochaku • Jizen Kosei Fuyona Chushiten Suitei," 'Meeting on Image Recognition and Understanding' (MIRU2011), pp. OS2-1:41 to OS2-1:48 (Jul. 2011).

Christian Nitschke et al., "Display-Camera Calibration from Eye Reflections," The Transactions of the Institute of Electronics, Information and Communication Engineers D, vol. J93-D, No. 8, pp. 1450-1460 (2010).

Taiwanese Office Action dated Sep. 3, 2014, issued in a counterpart patent application in Taiwan.

International Search Report mailed Aug. 20, 2013, in PCT/JP2013/070061, of which the present application is a U.S. national phase entry.

Ravi Kothari et al., "Detection of eye locations in unconstrained visual images", Proceedings of the International Conference on Image Processing (ICIP) Lausanne, Sep. 16-19, 1996, New York, IEEE, US, vol. 3, pp. 519-522.

Christian Nitschke et al., "Practical display-camera calibration from eye reflections using coded illumination", Pattern Recognition (ACPR), 2011 First Asian Conference on, IEEE, Nov. 28, 2011, pp. 550-554.

Feng Li et al., "Using Structured Illumination to Enhance Video-Based Eye Tracking", Proceedings 2000 International Conference on Image Processing (Cat. No. 00CH37101), Sep. 1, 2007, pp. I-373-I-376.

European Patent Office, "Extended European Search Report," issued in European Patent Application No. 13 826.471.8, which is a European Counterpart of U.S. Appl. No. 14/417,877, with an issuance date of Nov. 4, 2015, 5 pages.

* cited by examiner

|  | First condition (depth = 1900mm) | | Second condition (depth = 3000mm) | |
| --- | --- | --- | --- | --- |
|  | Method according to present invention | Interpolation | Method according to present invention | Interpolation |
| User 1 | 0.960 | 0.973 | 0.909 | 3.084 |
| User 2 | 0.960 | 0.973 | 0.909 | 3.084 |
| User 3 | 0.960 | 0.973 | 0.909 | 3.084 |
| User 4 | 0.960 | 0.973 | 0.909 | 3.084 |
| User 5 | 0.960 | 0.973 | 0.909 | 3.084 |
| Mean | 0.899 | 0.996 | 0.899 | 3.837 |

FIG. 13

POINT-OF-GAZE DETECTION DEVICE, POINT-OF-GAZE DETECTING METHOD, PERSONAL PARAMETER CALCULATING DEVICE, PERSONAL PARAMETER CALCULATING METHOD, PROGRAM, AND COMPUTER-READABLE STORAGE MEDIUM

CROSS REFERENCE TO RELATED APPLICATIONS

This patent application is a U.S. national stage application under 35 U.S.C. §371 of International Patent Application No. PCT/JP2013/070061 filed on Jul. 24, 2013, which claims the benefit of foreign priority to Japanese Patent Application No. JP 2012-169223 filed on Jul. 31, 2012. The International Application was published in Japanese on Feb. 6, 2014, as International Publication No. WO 2014/021169 A1 under PCT Article 21(2).

TECHNICAL FIELD

The present invention relates to point-of-gaze detection devices and point-of-gaze detecting methods for detection of a point-of-gaze of a subject toward a surrounding environment, personal parameter calculating devices and personal parameter calculating methods, programs, and computer readable storage mediums for calculation of a personal parameter indicative of a difference between a gaze direction of a subject and an optical axial direction of an eyeball of the subject.

BACKGROUND ART

Detection of a subject's point-of-gaze is a technique important for and essential to establishment of modern and next-generation information environments. Techniques relating to point-of-gaze detection have a wide range of applications, such as user interfaces, ubiquitous and ambient environments, human behavior recognition/understanding, communication analysis, etc., which use point-of-gaze information. Accordingly, various techniques have been reduced in practice in addition to implementation to commercially available products.

Non-patent Document 1 discloses a technique using an environment image reflected on the surface of an eyeball as a novel point-of-gaze detecting method. This technique achieves point-of-gaze detection by direct mapping between an environment image reflected on the surface of an eyeball and points of a scene captured by an environment camera. This technique has various advantages, such as: (1) system installation is easy; (2) the need of equipment fitting to a subject is eliminated; (3) a complicate depth-varying environment can be addressed; and the like.

CITATION LIST

Patent Document

[Non-patent Document 1] Nakazawa, Nitschke, Radcov, and Takemura, "Wear-free and Pre-calibration-free Point of Gaze Estimation Exploiting Eyeball Surface Reflection and High-speed Active Light Projection", Transaction of Meeting on Image Recognition and Understanding (MIRU 2011), Vol. 2011, pp. 41-48 (2011)

SUMMARY OF INVENTION

Technical Problem

The technique disclosed in Non-patent Document 1 needs a scheme for obtaining a reflection point at which incoming light in a gaze direction is reflected on the surface of an eyeball. Comparison between an image characteristic at the reflection point in an eyeball image and an image characteristic of an environment image can result in estimation of a point-of-gaze in the environment.

It is assumed in this technique that the optical axis direction of an eyeball is aligned with the gaze direction of a subject. However, actually, because the optical axis direction of the eyeball and the gaze direction of the subject differ on an individual basis, accuracy of the point-of-gaze estimation is limited.

The present invention has been made in view of the foregoing and has the object of providing a point-of-gaze detection device, a point-of-gaze detecting method, a personal parameter calculating device, a personal parameter calculating method, a program, and a computer readable storage medium, which take account of a personal parameter indicative of a difference between the gaze direction of a subject and the optical axis direction of an eyeball of the subject.

Solution to Problem

A point-of-gaze detection device according to the present invention is a point-of-gaze detection device to detect a point-of-gaze of a subject toward a surrounding environment. The device includes: an eyeball image obtaining means configured to obtain an eyeball image of the subject; a reflection point estimating means configured to estimate a first reflection point, at which incoming light in an optical axis direction of an eyeball of the subject is reflected, from the eyeball image; a corrected reflection point calculating means configured to calculate a corrected reflection point as a corrected first reflection point by correcting the first reflection point on the basis of a personal parameter indicative of a difference between a gaze direction of the subject and the optical axis direction of the eyeball; and a point-of-gaze detecting means configured to detect the point-of-gaze on the basis of light at the corrected reflection point and light in the surrounding environment.

In one embodiment, the point-of-gaze detection device further includes a pose calculating means configured to calculate a pose of the eyeball from the eyeball image. The reflection point estimating means estimates the first reflection point on the basis of the pose of the eyeball and a geometric model of the eyeball.

In one embodiment, the reflection point estimating means estimates the first reflection point on the basis of a model on the assumption that the gaze direction of the subject is parallel to the optical axis direction of the eyeball of the subject.

In one embodiment, the light in the surrounding environment is light of an LED array projector.

In one embodiment, the light in the surrounding environment is light of a pattern illumination marker.

A point-of-gaze detecting method according to the present invention is a point-of-gaze detecting method for detecting a point-of-gaze of a subject toward a surrounding environment. The method includes: obtaining an eyeball image of the subject; estimating a first reflection point, at which incoming light in an optical axis direction of an eyeball of the subject is reflected, from the eyeball image; calculating a corrected reflection point as a corrected first reflection point by correcting the first reflection point on the basis of a personal parameter indicative of a difference between a gaze direction of the subject and the optical axis direction of the eyeball; and detecting the point-of-gaze on the basis of light at the corrected reflection point and light in the surrounding environment.

A personal parameter calculating device according to the present invention is a personal parameter calculating device to calculate a personal parameter indicative of a difference between a gaze direction of a subject and an optical axis direction of an eyeball of the subject. The device includes: an eyeball image obtaining means configured to obtain an eyeball image of the subject; a reflection point estimating means configured to estimate a first reflection point, at which incoming light in the optical axis direction of the eyeball is reflected, from the eyeball image; a reflection point detecting means configured to detect a second reflection point, at which light coming from a point-of-gaze of the subject is reflected, from the eyeball image; and a personal parameter calculating means configured to calculate the personal parameter of the subject based on the first reflection point and the second reflection point.

In one embodiment, the personal parameter calculating device further includes a pose calculating means configured to calculate a pose of the eyeball from the eyeball image. The reflection point estimating means estimates the first reflection point on the basis of the pose of the eyeball and a geometric model of the eyeball.

In one embodiment, the reflection point estimating means estimates the first reflection point on the basis of a model on the assumption that the gaze direction of the subject is parallel to the optical axis direction of the eyeball for the subject.

A personal parameter calculating method according to the present invention is a personal parameter calculating method for calculating a personal parameter indicative of a difference between a gaze direction of a subject and an optical axis direction of an eyeball of the subject. The method includes: obtaining an eyeball image of the subject; estimating a first reflection point, at which incoming light in an optical axis direction of the eyeball is reflected, from the eyeball image; detecting a second reflection point, at which light coming from a point-of-gaze of the subject is reflected, from the eyeball image; and calculating the personal parameter of the subject on the basis of the first reflection point and the second reflection point.

A program according to the present invention is a program to allow a computer to execute point-of-gaze detection for detection of a point-of-gaze of a subject toward a surrounding environment. The program includes: obtaining an eyeball image of the subject; estimating a first reflection point, at which incoming light in an optical axis direction of an eyeball of the subject is reflected, from the eyeball image; calculating a corrected reflection point as a corrected first reflection point by correcting the first reflection point on the basis of a personal parameter indicative of a difference between a gaze direction of the subject and the optical axis direction of the eyeball; and detecting the point-of-gaze on the basis of light at the corrected reflection point and light in the surrounding environment.

A program according to the present invention is a program to allow a computer to execute personal parameter calculation for calculation of a personal parameter indicative of a difference between a gaze direction of a subject and an optical axis direction of an eyeball of the subject. The program includes: obtaining an eyeball image of the subject; estimating a first reflection point, at which incoming light in the optical axis direction of the eyeball is reflected, from the eyeball image; detecting a second reflection point, at which light coming from a point-of-gaze of the subject is reflected, from the eyeball image; and calculating the personal parameter of the subject on the basis of the first reflection point and the second reflection point.

A computer readable storage medium according to the present invention is a computer readable storage medium which stores a program to allow a computer to execute point-of-gaze detection for detection of a point-of-gaze of a subject toward a surrounding environment. The program includes: obtaining an eyeball image of the subject; estimating a first reflection point, at which incoming light in an optical axis direction of an eyeball of the subject is reflected, from the eyeball image; calculating a corrected reflection point as a corrected first reflection point by correcting the first reflection point on the basis of a personal parameter indicative of a difference between a gaze direction of the subject and the optical axis direction of the eyeball; and detecting the point-of-gaze on the basis of light at the corrected reflection point and light in the surrounding environment.

A computer readable storage medium according to the present invention is a computer readable storage medium which stores a program to allow a computer to execute personal parameter calculation for calculation of a personal parameter indicative of a difference between a gaze direction of a subject and an optical axis direction of an eyeball of the subject. The program includes: obtaining an eyeball image of the subject; estimating a second reflection point, at which incoming light in the optical axis direction of the eyeball is reflected, from the eyeball image; detecting a first reflection point, at which light coming from a point-of-gaze of the subject is reflected, from the eyeball image; and calculating the personal parameter of the subject on the basis of the first reflection point and the second reflection point.

BRIEF DESCRIPTION OF DRAWINGS

FIG. 13 is a table indicating errors in estimated angles of points-of-gaze.

DESCRIPTION OF EMBODIMENTS

Embodiments of a point-of-gaze detection device, a point-of-gaze detecting method, a personal parameter calculating device, and a personal parameter calculating method according to the present invention will be described below with reference to the accompanying drawings. It should be noted that the present invention is not limited to the following embodiments.

Embodiment 1

Point-of-Gaze Detection

Figure 1:
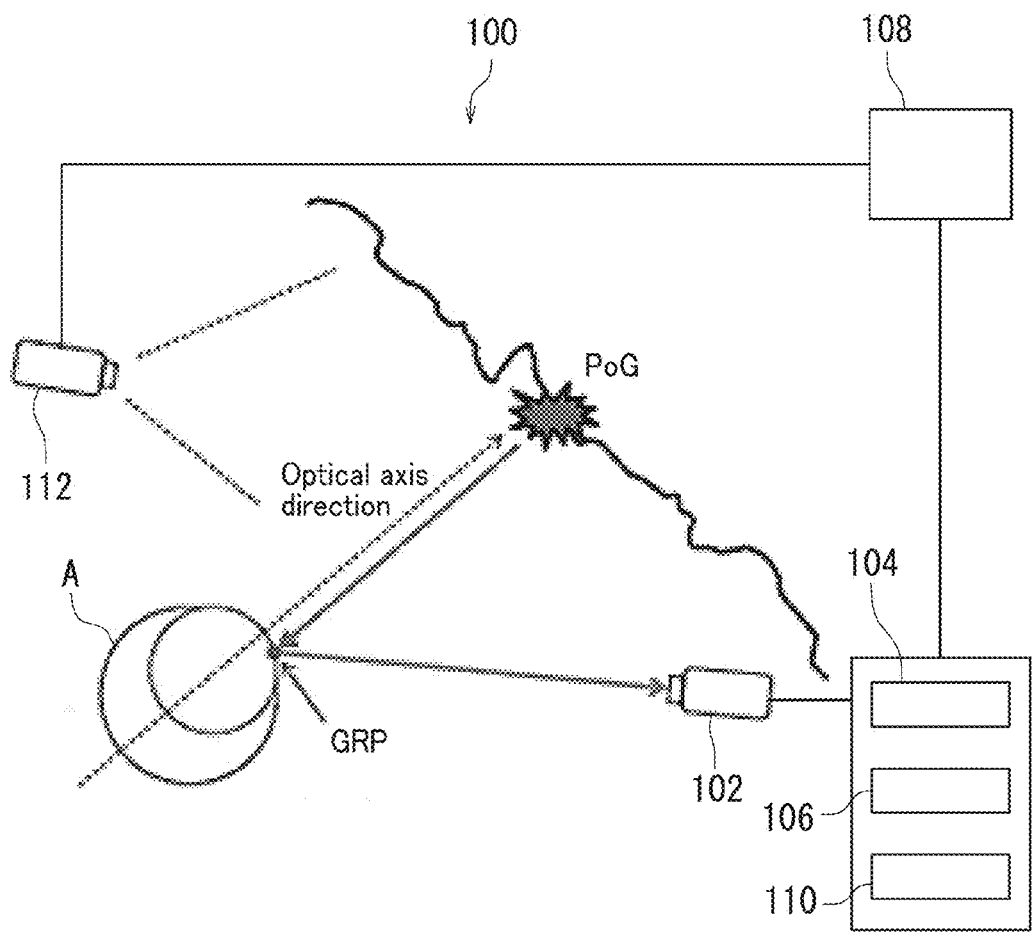
FIG. 1 is a schematic illustration showing a point-of-gaze detection device according to Embodiment 1 of the present invention.

FIG. 1 is a schematic illustration showing a point-of-gaze detection device 100 according to Embodiment 1 of the present invention. The point-of-gaze detection device 100 detects a point-of-gaze PoG of a subject A toward a surrounding environment. The surrounding environment means space surrounding the subject A and may be space expressed by X-Y coordinates or may be space expressed by XYZ coordinates. The point-of-gaze detection device 100 includes an eyeball image obtaining means 102 to obtain an image of an eyeball of the subject A, a reflection point estimating means 104, a corrected reflection point calculating means 106, and a point-of-gaze detecting means 108. The point-of-gaze detection device 100 further includes an environment light detecting device 112.

The eyeball image obtaining means 102 may be, for example, a digital camera, a CCD camera, or a pan-tilt-zoom camera, and is capable of detecting light in a visible light region. The eyeball image obtaining means 102 obtains an image of a static or moving eyeball of the subject A. The reflection point estimating means 104 estimates a first reflection point (gaze reflection point) GRP, at which incoming light in the optical axis direction of the eyeball of the subject A is reflected, from the eyeball image. The point-of-gaze detection device 100 may further include a pose calculating means 110 to calculate a pose of the eyeball from the eyeball image.

The reflection point estimating means 104 estimates the first reflection point GRP from the eyeball image on the basis of the pose of the eyeball and a geometric model of the eyeball.

The corrected reflection point calculating means 106 calculates a corrected reflection point (corrected GPR) cGPR as a corrected first reflection point by correcting the first reflection point GRP on the basis of a personal parameter indicative of a difference between a gaze direction of the subject A and the optical axis direction of the eyeball.

The environment light detecting device 112 may be, for example, a digital camera, a CCD camera, or a pan-tilt-zoom camera, and can detect light in the visible light region. The environment light detecting device 112 can detect light in the surrounding environment of the subject A, at which the subject A gazes. The light in the surrounding environment forms an image of the surrounding environment. The point-of-gaze detecting means 108 detects the point-of-gaze PoG on the basis of light at the corrected reflection point cGRP and the light in the surrounding environment. For example, the point-of-gaze detecting means 108 detects the point-of-gaze PoG by comparing the light at the corrected reflection point cGRP calculated by the corrected reflection point calculating means 106 and the light in the surrounding environment detected by the environment light detecting device 112.

The reflection point estimating means 104, the corrected reflection point calculating means 106, the point-of-gaze detecting means 108, and the pose calculating means 110 may be electronic computers, such as personal computers, or the like, for example.

It is noted that although the point-of-gaze detecting means 108 detects the point-of-gaze PoG on the basis of the light at the corrected reflection point cGRP and the light in the surrounding environment, the light in the surrounding environment is not limited to that detected by the environment light detecting device 112.

For example, the point-of-gaze detection device 100 may include a projection means and a projected light detecting means in lieu of the environment light detecting device 112. The projection means includes a light source to project light on the surrounding environment. The projection means may be a projector, for example. The projection means projects, for example, visible light showing scenery in the surrounding environment, visible light indicating a gray coded pattern, or the like. As will be described in detail with reference to FIGS. 7A and 7B, the projection means may be an LED array projector. Where the surrounding environment is a wall of a room, the projection means projects the light on the wall of the room. Where the surrounding environment is a rock wall of a mountain, the projection means projects the light on the bumpy rock wall. Further, in the case where the projection means is a three-dimensional video system, it can project a realistic three-dimensional video image formed of dot arrays in space with nothing except air.

The projected light detecting means detects projected light projected from the projection means. The projected light detecting means may be, for example, a digital camera or a CCD camera, and can detect light in a visible light region. The point-of-gaze detecting means 108 detects the point-of-gaze PoG by comparing the light at the corrected reflection point cGRP calculated by the corrected reflection point calculating means 106 and the projected light detected by the projected light detecting means.

Further, for example, the point-of-gaze detection device 100 may include a display means in lieu of the environment light detecting device 112. The display means displays the light in the surrounding environment. The display means may be a display panel, a monitor screen, or the like, which emits light. As will be described in detail with reference to FIGS. 7A and 7B, the display means may be a pattern illumination marker. The light in the surrounding environment is transmitted to the point-of-gaze detecting means 108 as display image data displayed on the display means. The point-of-gaze detecting means 108 detects the point-of-gaze PoG by comparing the light at the corrected reflection point cGRP calculated by the corrected reflection point calculating means 106 and the light of the displayed image displayed on the display means.

Figure 2:
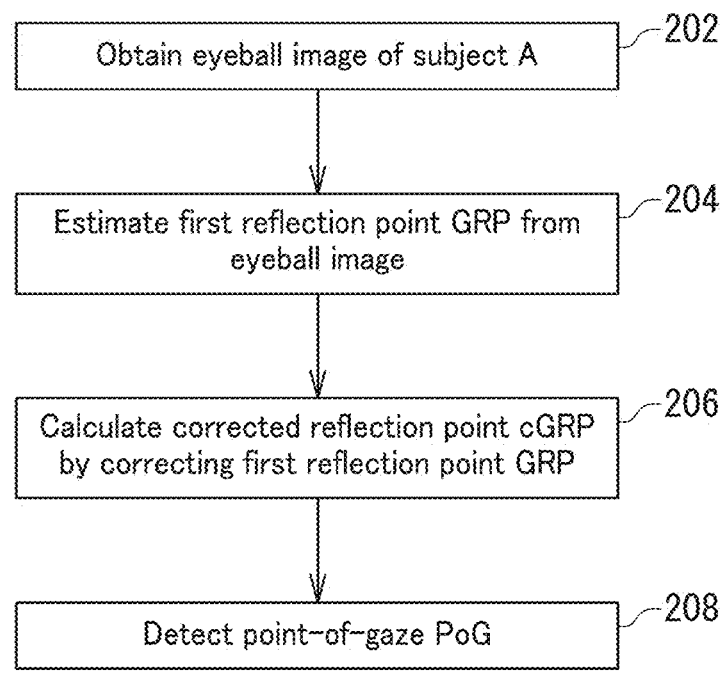
FIG. 2 is a flowchart depicting an operation of the point-of-gaze detection device according to Embodiment 1 of the present invention.

FIG. 2 is a flowchart depicting an operation of the point-of-gaze detection device 100. With reference to FIGS. 1 and 2, a point-of-gaze detecting method will be described. As will be described below, the point-of-gaze detection device 100 executes a step 202 through to a step 208 to achieve point-of-gaze detection according to Embodiment 1 of the present invention.

Step 202: The eyeball image obtaining means 102 obtains an eyeball image of the subject A.

Step 204: The reflection point estimating means 104 estimates a first reflection point GRP, at which incoming light in the optical axis direction of the eyeball of the subject A is reflected, from the eyeball image.

Step 206: The corrected reflection point calculating means 106 calculates a corrected reflection point cGRP as a corrected first reflection point by correcting the first reflection point GRP on the basis of a personal parameter.

Step 208: The point-of-gaze detecting means 108 detects a point-of-gaze PoG on the basis of the light at the corrected reflection point cGRP and the light in the surrounding environment.

It is noted that a device to perform point-of-gaze detection is not limited to the point-of-gaze detection device 100. The point-of-gaze detection device 100 can be any device as far as it has the functions of the eyeball image obtaining means 102, the reflection point estimating means 104, the corrected reflection point calculating means 106, and the point-of-gaze detecting means 108. For example, the point-of-gaze detecting method can be implemented by a personal computer. Alternatively, it can be implemented by a personal computer that forms part of the point-of-gaze detection device 100.

Where the point-of-gaze detecting method is implemented by a personal computer, the point-of-gaze detecting method is performed through execution of a point-of-gaze detection program. The personal computer includes a memory and a CPU. The memory stores the point-of-gaze detection program. The CPU reads the point-of-gaze detection program from the memory and controls a means having the function of the eyeball image obtaining means 102 and a means having the function of the reflection point estimating means 104 so that the means having the function of the eyeball image obtaining means 102 executes the step 202 and so that the means having the function of the reflection point estimating means 104 executes the step 204.

The CPU further reads the point-of-gaze detection program from the memory and controls a means having the function of the corrected reflection point calculating means 106 and a means having the function of the point-of-gaze detecting means 108 so that the means having the function of the corrected reflection point calculating means 106 executes the step 206 and so that the means having the function of the point-of-gaze detecting means 108 executes the step 208.

By reading out the point-of-gaze detection program from a storage medium outside the personal computer, which stores the point-of-gaze detection program, the point-of-gaze detection program can be installed in the memory of the personal computer. Any medium, such as a flexible disc, CD-ROM, CD-R, DVD, MO, etc., can be used as the storage medium outside the personal computer. Alternatively, the point-of-gaze detection program can be installed in the memory of the personal computer by downloading the point-of-gaze detection program via any network, such as the Internet.

Figure 3A:
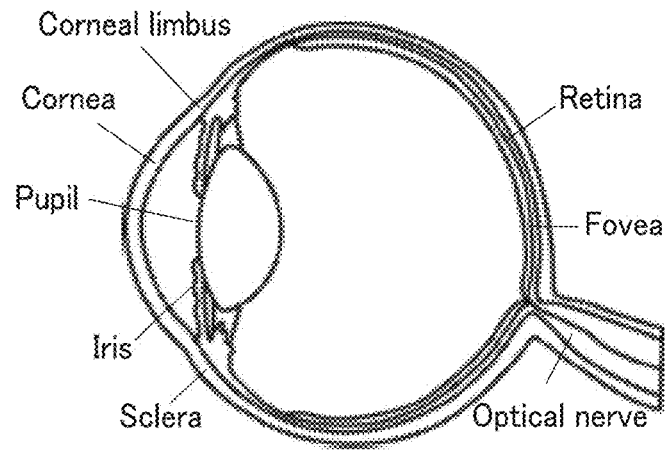
FIG. 3A is a schematic illustration of an eyeball.
Figure 3B:
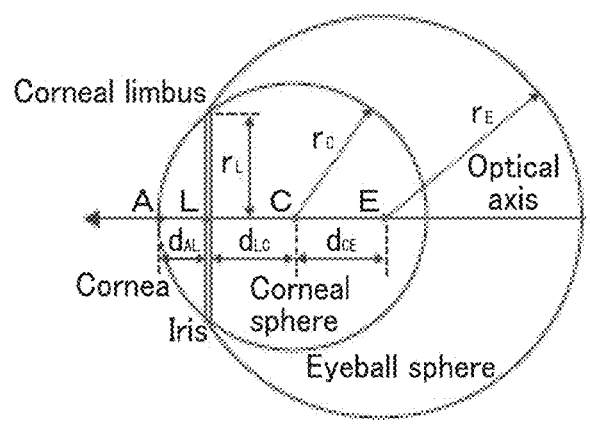
FIG. 3B is a schematic illustration of an approximate geometric model of an eyeball.

The point-of-gaze detection device 100 and the point-of-gaze detecting method will be described in detail below. In the present embodiment, a geometric model of an eyeball is introduced. FIG. 3A is a schematic illustration of an eyeball. FIG. 3B shows an approximate geometric model of an eyeball. The eyeball is not a single sphere but is approximately formed of two different spheres, of a sphere of cornea (corneal sphere) and of the eyeball itself (eyeball sphere). The approximate geometric model uses known values (iris radius $r_L$=5.6 mm and corneal radius $r_C$=7.7 mm). The approximate geometric model is geometrically simple and therefore is easy to handle analytically. It is considered that the approximate geometric model can exhibit sufficient accuracy in analysis of reflection of an eyeball surface.

Prior to estimation of the first reflection point GRP from the eyeball image, the pose of the eyeball is estimated in the present embodiment. The pose calculating means 110 detects a pupil boundary and an iris boundary and calculates the pose of the eyeball from the eyeball image. The pupil boundary and the iris boundary are detected using infrared light. First, a pupil region is extracted by the dark pupil method. The dark pupil method is a method that exploits a difference in light reflection/absorption characteristics between a pupil and the other region. The following document can be referenced in detail.

R. Kothari and J. L. Mitchell: "Detection of eye locations in unconstrained visual images", Proc. Int. Conf. on Image Processing (ICIP), pp. 519-522 (1996).

Figures 4A, 4B, 4C:
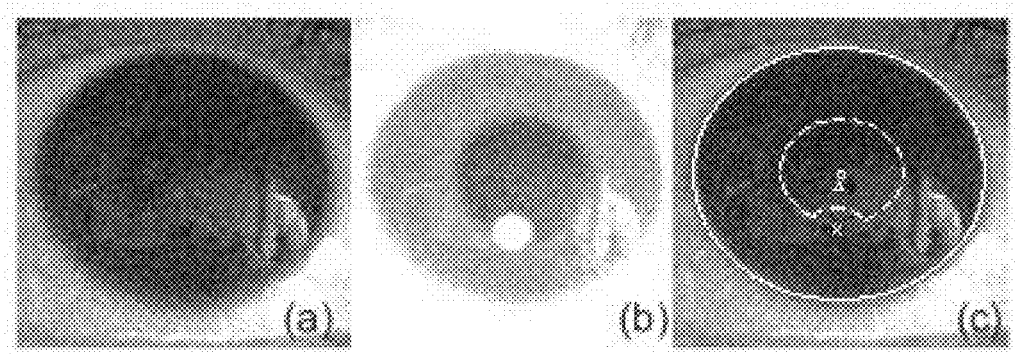
FIGS. 4A-4C show detection results of an iris boundary by a dark pupil method.

FIGS. 4A-4C indicate results of detection of an iris boundary by the dark pupil method. FIG. 4A shows a first frame. FIG. 4B shows a second frame (infrared light lighting). FIG. 4C shows results of detection of a pupil and an iris boundary. In FIG. 4C, the white solid line indicates the iris boundary. The white dotted line inside the white solid line indicates the pupil boundary obtained by the dark pupil method. The white circle indicates the center of the iris boundary. The white x-mark indicates the center of the corneal sphere. The white triangle indicates the first reflection point GRP.

An infrared LED mounted on the eyeball image obtaining means 102 is switched off in the first frame and switched on in the second frame. In the eyeball region, the pupil absorbs light from outside to be projected black in both frames. However, the other region reflects the light to be projected bright in the second frame. By taking the difference between the first frame and the second frame of the projected images, a region having a smaller value can be regarded as a pupil region.

Figure 5:
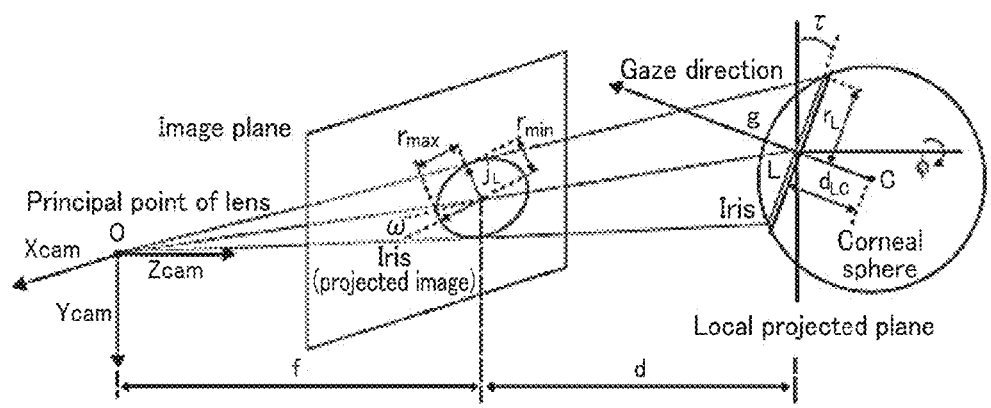
FIG. 5 is a schematic illustration for explaining eyeball pose estimation from a projected image of an iris.

FIG. 5 is a schematic illustration for explaining eyeball pose estimation from the projected image of the iris. Description will be continued with reference to FIG. 5. RANSAC-based ellipse fitting is applied to the boundary of the pupil region to obtain an ellipse B (x, y, $c_x$, $c_y$, a, b, $\phi$). Here, ($c_x$, $c_y$) indicates the center. Reference characters a, b, and $\phi$ denote a minor axis, a major axis, and an angle of rotation, respectively. Two-step minimization is performed using the results of estimation of the pupil boundary to estimate the iris boundary.

Step 51: Only the parameter (a, b) of the radius is changed using the center and the angle of rotation ($c_s$, $c_y$, $\phi$) of the pupil to maximize the following function, thereby obtaining initial parameters $a_0$, $b_0$ of the radius of the iris.

[Equations 1]

$$\text{eval}(c_x, c_y, a, b, \phi) = \sum_{x,y} E_x(x, y) \cdot \text{sgn}(c_x - x) \cdot B(x, y, c_x, c_y, a, b, \phi). \quad (1)$$

$$[a_0, b_0] = \underset{a,b}{\text{argmax}}\, \text{eval}(c_x, c_y, a, b, \phi). \quad (2)$$

Where $E_x(x, y)$ is an x derivative of an input image. Also, $a_0$>a and $b_0$>b. Only the x derivative of the image is used in order to avoid influence of the eyelid. Further, sgn($c_x$-x) is used for evaluation of the fact that the iris is changed over to the white of the eye as a point goes from the center coordinate of the iris toward the outside.

Step S2: All the parameters of the ellipse are converged by the same evaluation function with the use of the initial parameters of the obtained radius to obtain parameters ($c'_x$, $c'_y$, $a'$, $b'$, $\phi'$) of the iris boundary.

Using these parameters can result in obtaining the gaze direction g by the following equation (3).

[Equation 2]

$$g = [\sin\tau\sin\phi, -\sin\tau\cos\phi, -\cos\tau]^T \quad (3)$$

Here, $\tau$ denotes an inclination of the depth direction of the eye and can be obtained by $\tau = \pm\arccos(r_{min}/r_{max})$. Further, from the above, the center point C of the corneal sphere can be obtained using a known length $d_{LC}$ (=5.6 mm) from L to C and a gaze vector g.

The reflection point estimating means 104 estimates a point (first reflection point GRP), at which light incident from the point-of-gaze PoG is reflected on the eyeball sphere, with the use of the obtained three-dimensional pose of the eyeball. Shooting a reflection image of the eyeball surface by the eyeball image obtaining means 102 can be regarded as that by a catadiopic system. The first reflection point GRP can be obtained using the geometric model of the corneal sphere as a reflection sphere and the eyeball pose obtained from the eyeball image obtaining means 102. Non-patent Document 1 discloses a perspective projection model and a weak perspective projection model as an estimation model of a first reflection point GRP.

Figure 6A:
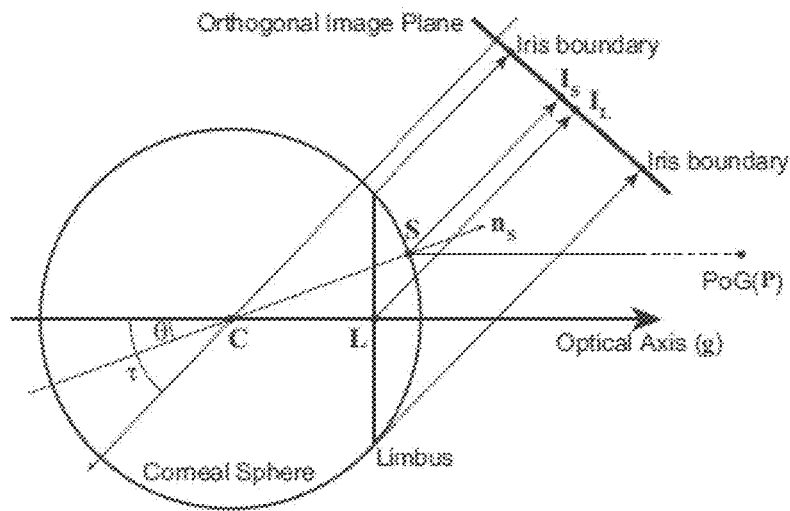
FIGS. 6A and 6B present schematic illustrations showing the relationship between surface reflection and a reflection point of an eyeball.

Description will be made about an example exploiting a weak perspective projection model as a model of the first reflection point GRP in the present embodiment. It can be supposed that entering and reflection of light at the eyeball surface occur on a single plane. In the case using the weak perspective projection model, this plane includes a minor axis of the iris of the projected image (ellipse) and is orthogonal to the image plane. When it is assumed that light coming from the point-of-gaze PoG of the subject A is incoming light in the optical axis direction of the eyeball, the light beam path is as shown in FIG. 6A. FIG. 6A shows the state in which light coming from the point-of-gaze PoG of the subject A in parallel to the gaze direction (the optical axis direction of the eyeball) is reflected on the surface of the cornea to enter the eyeball image obtaining means 102. By referring to FIG. 6A, the following equations can be obtained using the relationship of the reflection on the surface of the cornea.

[Equations 3]

$$C \cdot n_S = g \cdot n_S, C = [01]^T,$$

$$g = [\cos\tau \sin\tau]^T, n_S = [\cos\theta \sin\theta]^T. \quad (4)$$

From the equations, the angle $\theta$ indicating the first reflection point GRP can be obtained using $\tau$ indicating the optical axis direction of the eyeball.

[Equation 4]

$$\theta = \arctan((1-\sin\tau)/\cos\tau) \quad (5)$$
$$= \tau/2.$$

Further, the distance $|I_S - I_L|$ between the center of the iris and the first reflection point GRP on a local projected plane by weak perspective projection can be obtained as follows.

[Equation 5]

$$|I_S - I_L| = r_c \sin\theta - d_{LC}\sin\tau. \quad (6)$$

Next, given the weak perspective projection regarding the center of the iris as an object center, the position $i_s$ of the first reflection point GRP in the eyeball image can be obtained as follows.

[Equations 6]

$$i_S = i_L + s \cdot v_{sm}|I_S - I_L|, s = r_{max}/r_L, \quad (7)$$

Here, s denotes a scale factor of the weak perspective projection; $i_L$ denotes a coordinate of the center of the iris; and $v_{sm}$ denotes a two-dimensional vector indicating the minor axis of the projected image (ellipse) of the iris.

The corrected reflection point calculating means 106 rotates the iris center coordinate system Re, which is obtained by eyeball pose estimation, by a personal parameter ($\delta x$, $\delta y$) to correct the first reflection point GRP, thereby calculating the corrected reflection point cGRP as a corrected first reflection point. The specific process is as follows.

[Equations 7]

$$\tau^* = \arccos(e_z^T R_e^* e_z), \quad (8)$$

$$v_{sm}^* = \left(\begin{bmatrix} e_x^T \\ e_y^T \end{bmatrix} R_e^* e_y\right) / \left|\begin{bmatrix} e_x^T \\ e_y^T \end{bmatrix} R_e^* e_y\right| \quad (9)$$

$$R_e^* = R_x(\delta x) R_y(\delta y) R_e, \quad (10)$$

Here, $R_x$ and $R_y$ denote matrices indicating rotation about the x axis and the y axis, respectively. By substituting $\tau^*$ obtained herein for $\tau$ in Equations (6) and additionally substituting $v_{sm}^*$ for $v_{sm}$ in Equations (7), one can obtain the corrected reflection point cGRP.

The point-of-gaze detecting means 108 detects the point-of-gaze PoG on the basis of the light at the corrected reflection point cGRP and light in the surrounding environment. For example, the point-of-gaze detecting means 108 maps digital data indicating the light at the corrected reflection point cGRP to the digital data indicating the light in the surrounding environment to detect the point-of-gaze PoG included in the surrounding environment from the mapped digital data. It is noted that the point-of-gaze PoG of the subject A in the present specification indicates a point, a region, or a part where the subject A gazes.

For example, in the present embodiment, digital data indicating the light in the surrounding environment can be obtained by adopting an active-light method. The active-light method can be implemented by, for example, mounting an LED array projector (LED-AP) or a pattern illumination marker.

Figure 7A:
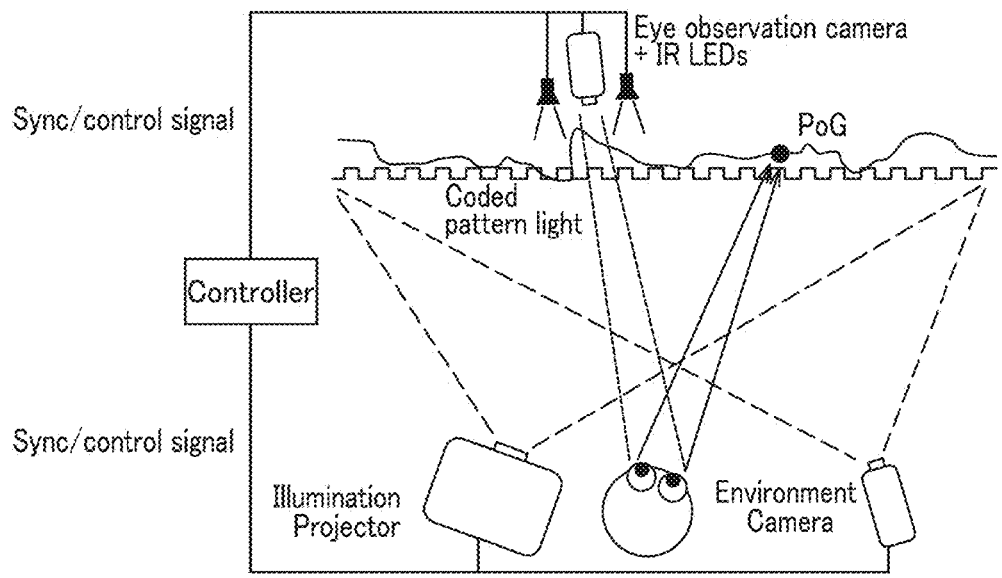
FIGS. 7A and 7B present schematic illustrations showing a system configuration using a LED-AP and a system configuration using a pattern illumination marker.
Figure 7B:
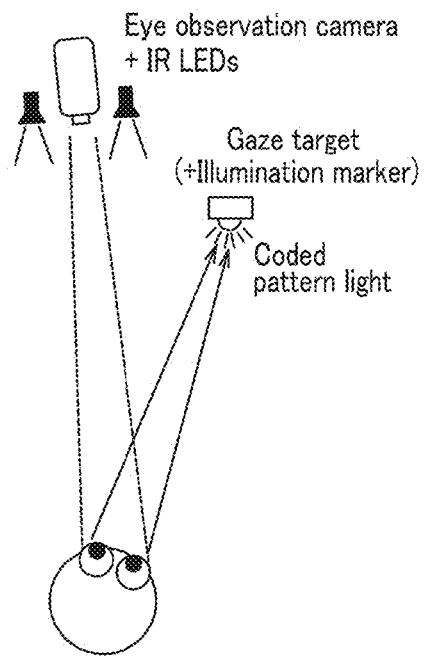

FIGS. 7A and 7B show a system configuration using an LED-AP and a system configuration using a pattern illumination marker. FIG. 7A shows the system configuration using the LED-AP, by which light is projected on a scene at high speed. When the eyeball image obtaining means 102 obtains reflected light projected on the eyeball surface, the point-of-gaze PoG can be estimated. This means that the point-of-gaze GoP can be obtained as an arbitrary point in the scene.

FIG. 7B shows the system configuration using the pattern illumination marker. In this configuration, the marker is mounted on a gaze target so that whether the subject gazes at the target or which of a plurality of targets the subject gazes at is determined. The gaze information is obtained on a targetby-target basis. However, point-of-gaze estimation can be achieved with further simple configuration only by mounting a small marker on each target. Further, easy analysis thereafter on the obtained gaze data can be facilitated.

Figure 8A:
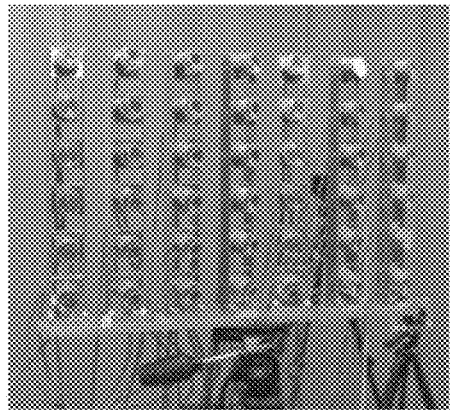
FIGS. 8A-8D present photographs showing a configuration of the LED-AP.
Figure 8B:
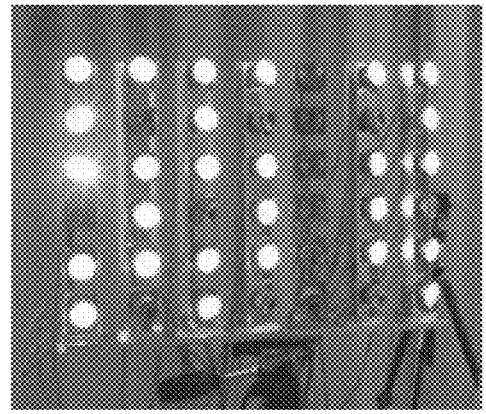
Figure 8C:
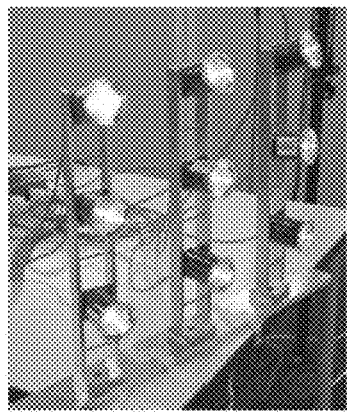
Figure 8D:
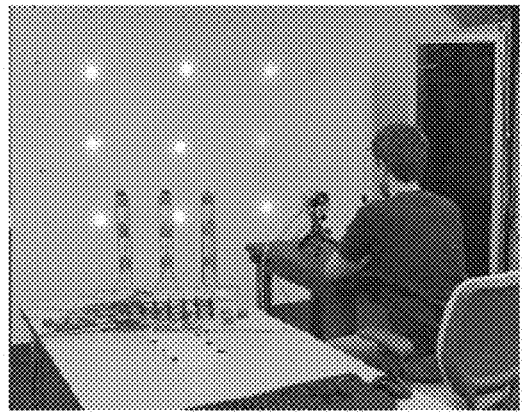

FIGS. 8A-8D show a configuration of the LED-AP. FIG. 8A shows an LED array (42 LEDs) unit, which includes high luminance LEDs (visible light or infrared light) and a Fresnel lens for light condensation. FIG. 8B shows an LED array (9 LEDs) unit. FIGS. 8C and 8D each show an experiment environment and a light pattern.

The LED-AP includes a high luminance LED group in which LEDs are arranged in a lattice fashion, a lens, and a controller. Each LED is controllable for 0.05-ms lighting. The LEDs can project light in a two-value pattern along different timelines. Further, since the direction of the LEDs can be changed independently, light can be arranged so as to reach a wide range.

Figures 9A, 9B, 9C:
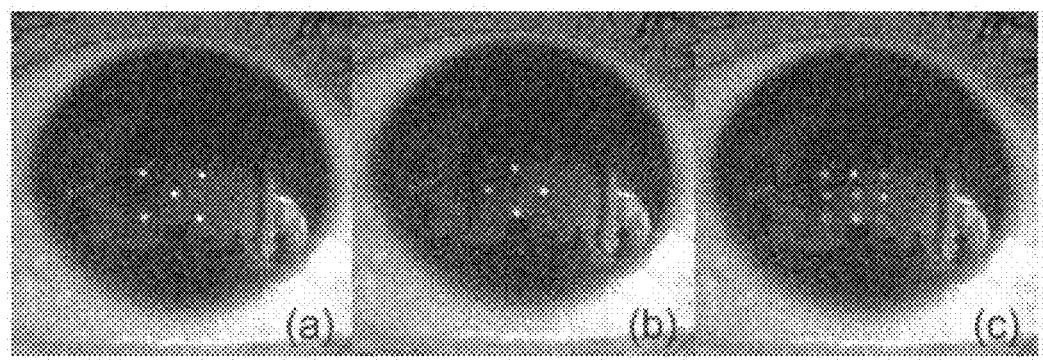
FIGS. 9A-9C present schematic illustrations for explaining identification of LEDs as light sources.

When a unique ID is allotted to the light pattern along the timeline of each LED, any ID can be reproduced from an image string captured by a camera to identify the LED as a light source (FIGS. 9A-9C). By contrast, the spatial resolution in an environment depends on the number of LEDs and accordingly is limited. In order to address this problem, the point-of-gaze PoG is estimated in combination with linear interpolation. That is, projection points of three LEDs near the first reflection point GRP are obtained in the eyeball reflection image. Then, the relative positional relationship between the projection points of the three LEDs and the first reflection point GRP is obtained. A projection point of each LED in the environment image is also obtained. Then, the point-of-gaze PoG in the environment image is estimated using the already obtained relative positional relationship with the first reflection point GRP. The process flow is as follows.

First, a timeline code is reproduced from a sequence of eyeball reflection images to obtain an ID for each pixel. Labeling is performed on the basis of the reproduced IDs. Labels having a predetermined or larger area are obtained. Then, the position of their center of gravity is set as a surface reflection point against the LEDs. Visible light LEDs or infrared LEDs are employed in the LED-AP. This enables estimation of the point-of-gaze PoG without projected light being noticed by the subject A.

Figures 10A, 10B:
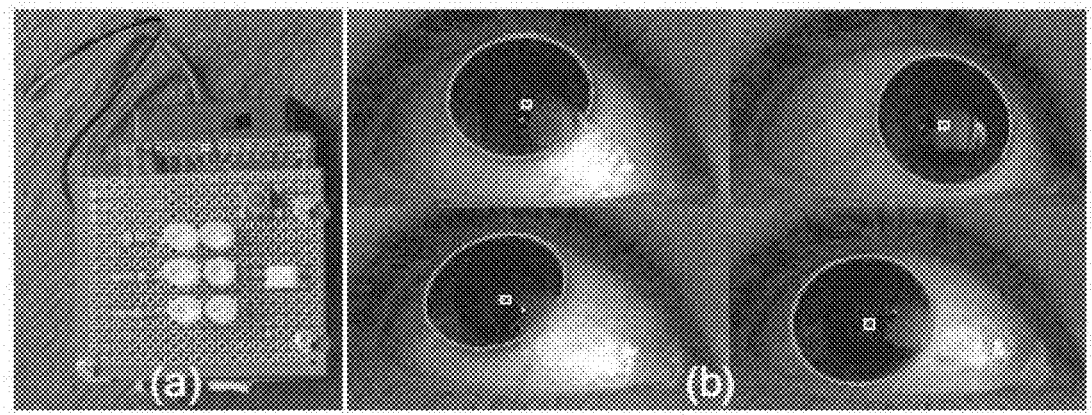
FIGS. 10A and 10B present photographs showing a configuration of the pattern illumination marker and images reflected on eyeballs.

FIGS. 10A and 10B show a configuration of a pattern illumination marker and eyeball reflection images. As shown in FIG. 10A, the pattern illumination marker has a configuration such that LEDs of an LED-AP are independent, and includes a microcontroller and an infrared LED. LEDs of a plurality of the pattern illumination markers emit light in patterns along different timelines. When the marker is mounted on a gaze target, whether or not the subject A gazes at the gaze target can be determined.

FIG. 10B shows the state in which two types of objects move in front of the subject A. The pattern illumination marker is mounted on each object. Each white ellipse indicates an iris boundary. Each white rectangular frame indicates the first reflection point GRP. It can be understood that one of the pattern illumination markers agrees with the first reflection point GRP.

The microcontroller is mounted on each marker. Thus, synchronization with real time clock can maintain synchronization of the emission patterns. From the positional relationship between the first reflection point GRP and the corrected reflection point cGRP of each marker on the eyeball surface, the angle between the marker and the gaze direction can be calculated. Accordingly, angle threshold processing or the like can determine whether or not the subject gazes.

Embodiment 2

Personal Parameter Calculation

Figure 11:
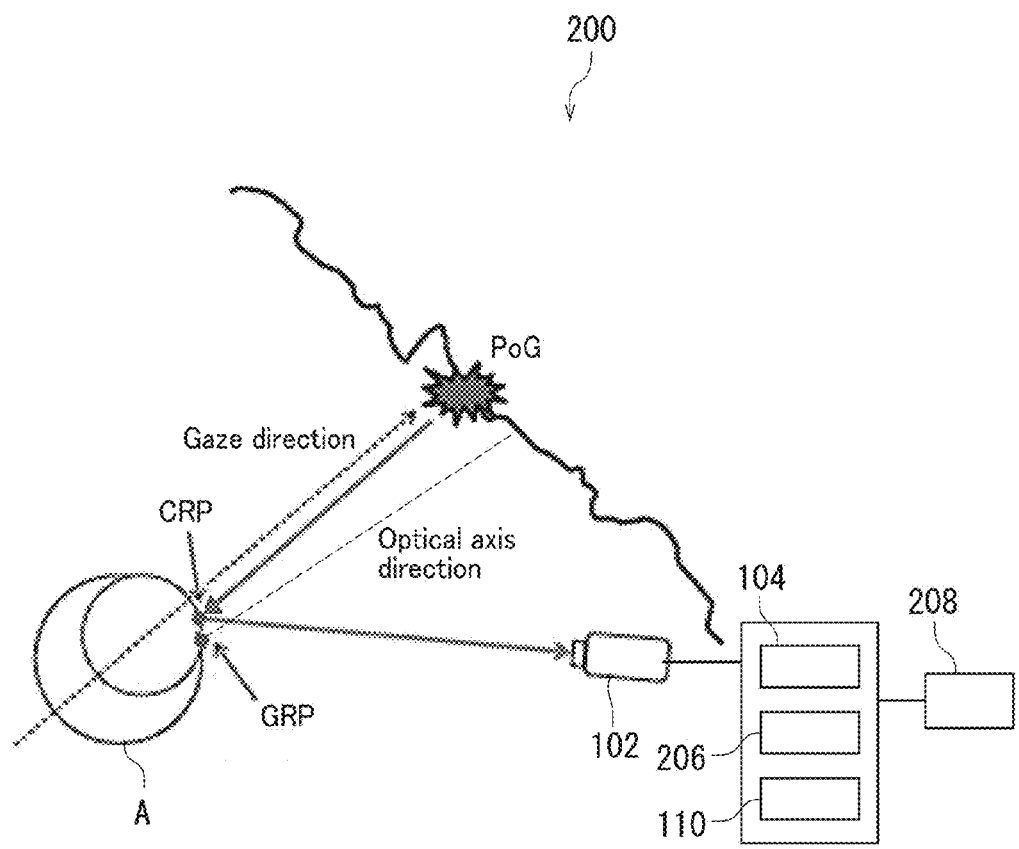
FIG. 11 is a schematic illustration of a personal parameter calculating device according to Embodiment 2 of the present invention.

FIG. 11 is a schematic illustration of a personal parameter calculating device 200 according to one embodiment of the present invention. The personal parameter calculating device 200 calculates a personal parameter indicative of a difference between a gaze direction of a subject A and an optical axis direction of an eyeball of the subject A. The personal parameter calculating device 200 includes an eyeball image obtaining means 102 to obtain an eyeball image of the subject A, a reflection point estimating means 104 to estimate a first reflection point GRP, at which incoming light in the optical axis direction of an eyeball is reflected, from the eyeball image, a reflection point detecting means 206 to detect a second reflection point CRP (calibration reflection point), at which light coming from a point-of-gaze PoG of the subject A is reflected, from the eyeball image, and a personal parameter calculating means 208 to calculate a personal parameter of the subject A on the basis of the first reflection point GRP and the second reflection point CRP.

It is noted that the eyeball image obtaining means 102 has the same function as the eyeball image obtaining means 102 described with reference to FIG. 1. The reflection point estimating means 104 has the same function as the reflection point estimating means 104 described with reference to FIG. 1. Accordingly, a detailed description thereof is omitted.

Figure 12:
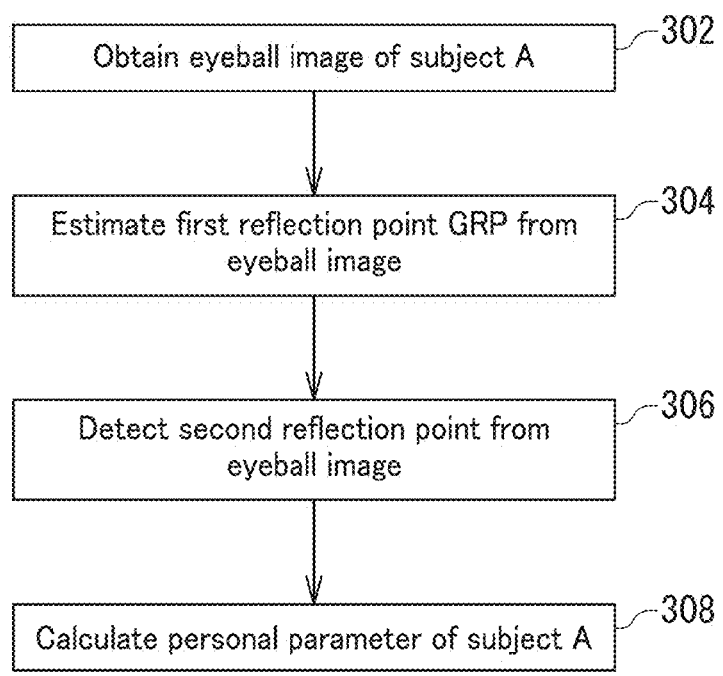
FIG. 12 is a flowchart depicting an operation of the personal parameter calculating device according to Embodiment 2 of the present invention.

FIG. 12 is a flowchart depicting an operation of the personal parameter calculating device 200. A personal parameter calculating method will be described with reference to FIGS. 11 and 12. As will be described below, when the personal parameter calculating device 200 executes a step 302 through to a step 308, personal parameter calculation according to Embodiment 2 of the present invention can be achieved.

Step 302: The eyeball image obtaining means 102 obtains an eyeball image of the subject A.

Step 304: The reflection point estimating means 104 estimates the first reflection point GRP from the eyeball image.

Step 306: The reflection point detecting means 206 detects the second reflection point CRP, at which light coming from the point-of-gaze PoG of the subject is reflected, from the eyeball image.

Step 308: The personal parameter calculating means 208 calculates a personal parameter of the subject A on the basis of the first reflection point GRP and the second reflection point CRP.

It is noted that a device to perform personal parameter calculation is not limited to the personal parameter calculating device 200. The device can be any device as far as it has the functions of the eyeball image obtaining means 102, the reflection point estimating means 104, the reflection point detecting means 206, and the personal parameter calculating means 208. For example, the personal parameter calculating method can be implemented by a personal computer. Further, it can be implemented by a personal computer that forms part of the personal parameter calculating device 200.

Where the personal parameter calculating method is implemented by a personal computer, the personal parameter calculating method is performed through execution of a personal parameter calculation program. The personal computer includes a memory and a CPU. The memory stores the personal parameter calculation program. The CPU reads the personal parameter calculation program from the memory and controls a means having the function of the eyeball image obtaining means 102 and a means having the function of the reflection point estimating means 104 so that the means having the function of the eyeball image obtaining means 102 executes the step 302 and so that the means having the function of the reflection point estimating means 104 executes the step 304.

The CPU further reads the personal parameter calculation program from the memory and controls a means having the function of the reflection point detecting means 206 and a means having the function of the personal parameter calculating means 208 so that the means having the function of the reflection point detecting means 206 executes the step 306 and so that the means having the function of the personal parameter calculating means 208 executes the step 308.

By reading out the personal parameter calculation program from a storage medium outside the personal computer, which stores the personal parameter calculation program, the personal parameter calculation program can be installed in the memory of the personal computer. Any medium, such as a flexible disc, CD-ROM, CD-R, DVD, MO, etc., can be used as the storage medium outside the personal computer. Alternatively, the personal parameter calculation program can be installed in the memory of the personal computer by downloading the personal parameter calculation program via any network, such as the Internet.

Detailed description will be made below about the personal parameter calculating device 200 and the personal parameter calculating method. The first reflection point GRP is estimated on the assumption that the gaze direction of the subject A agrees with the optical axis direction of the eyeball. However, it is suggested that the gaze direction of the subject A may not agree with the optical axis direction of the eyeball. The value of disagreement (personal parameter) between the gaze direction of the subject A and the optical axis direction of the eyeball depends on individuals and must be obtained in some way prior to estimation of the point-of-gaze.

Accordingly, similar to derivation of the first reflection point GRP, a method for calculating a personal parameter that exploits a reflection image of an eyeball surface is developed. Different from conventional calibration, this novel calibration method needs for the subject A only to gaze at one point in a scene. Thus, a burden on the subject A necessary for calibration can be relieved significantly.

The personal parameter is a fixed parameter defined by a face coordinate system. When the frontward direction of a face, a direction from the left eye to the right eye, and an axis orthogonal to both of them are denoted by $z_{face}$, $x_{face}$, and $y_{face}$, respectively, in a face coordinate system, the personal parameter is 1.5-3 degrees about the $x_{face}$ axis (tilt) and 4-5 degrees about the $y_{face}$ axis (pan) in terms of a rotation angel.

Figure 6B:
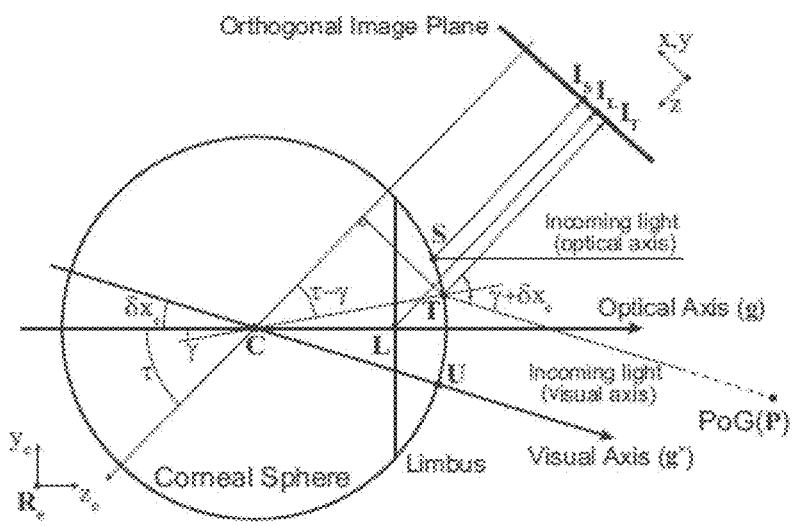

The coordinate system with an iris as a center is defined as Re=[$x_e$ $y_e$ $z_e$]. Here, $x_e$ and $y_e$ denote directions of a major axis and a minor axis in an iris image, respectively. FIG. 6B illustrates a plane ($y_e z_e$-plane) in the direction of the minor axis in a projected image of an iris. FIG. 6B shows a difference between the optical axis direction and the gaze direction of the eyeball. The gaze direction (g') of the subject A does not agree with the optical axis direction (g). The incoming light in the gaze direction is reflected at the corrected reflection point cGRP (T) and is projected on $I_T$ on the image.

The subject A gazes at a calibration point in the scene. Then, the eyeball image obtaining means 102 obtains an eyeball image of the subject A. The reflection point estimating means 104 estimates the first reflection point GRP from the eyeball image. When the reflection point detecting means 206 obtains the second reflection point CRP from the eyeball image, the personal parameter calculating means 208 can obtain an angle γ between the first reflection point GRP and the second reflection point CRP on this plane by the following equations.

[Equations 8]

$$|I_L - I_T| = \frac{|v_{sm} \cdot (i_T - i_L)|}{s}, \quad (11)$$

$$\gamma = \tau - \arcsin\left(d_{LC} \cdot \cos\tau + \frac{|I_L - I_T|}{r_C}\right), \quad (12)$$

Here, $I_T$ and $i_T$ denote the position of the second reflection point CRP and the projection point in the image, respectively.

When attention is directed to reflection at the second reflection point CRP on the eyeball surface, the personal parameter $\delta x_e$ in this plane can be obtained as follows.

[Equations 9]

$$2 \cdot (\gamma + \delta x_e) = \tau + \delta x_e, \quad (13)$$

$$\delta x_e = \tau - 2 \cdot \gamma. \quad (14)$$

Similarly, the personal parameter $\delta y_e$ in the plane orthogonal to this plane can be obtained as follows.

[Equation 10]

$$\delta y_e = 2 \cdot \arcsin\left(\frac{v_{lm} \cdot (i_T - i_L)}{s \cdot r_C}\right), \quad (15)$$

Here, $v_{lm}$ denotes a length of the major axis of the iris in the direction in the projected image.

In general, the eyeball image obtaining means 102 is set in front of the face. Accordingly, the personal parameter in terms of the face coordinate system obtained as above can be converted to a camera coordinate system by the following equations.

[Equation 11]

$$\delta x = \arctan\left(\frac{e_y^T R_e u}{e_z^T R_e u}\right), \quad (16)$$

$$\delta y = \arctan\left(\frac{e_x^T R_e u}{e_z^T R_e u}\right), \quad (17)$$

$$u = \begin{bmatrix} \sin\delta y_e & \sin\delta x_e & \sqrt{1 - \sin^2\delta x_e - \sin^2\delta y_e} \end{bmatrix}^T. \quad (18)$$

$$e_x = [1\ 0\ 0]^T, e_y = [0\ 1\ 0]^T, e_z = [0\ 0\ 1]^T.$$

When the personal parameter is obtained, the corrected reflection point cGRP can be obtained. The corrected reflection point cGRP can be obtained by only rotating the iris center coordinate system Re, which is obtained by eyeball pose estimation by the pose calculating means 110, by the personal parameter (δx, δy).

Example

In order to confirm the effectiveness of the embodiment of the present invention, point-of-gaze detection by interpolation frequently employed in commercially available systems was implemented in the point-of-gaze detection device besides the embodiment of the present invention. Then, comparison was made therebetween. The point-of-gaze detection by interpolation, which is a method frequently employed in commercially available systems, uses two types of infrared light sources. One of the light sources is used for pupil detection by the dark pupil method. The other light source is a point light source (CAM-LED) used for obtaining reflection on an eyeball surface. By using them, the gaze direction is obtained from the relative positional relationship between the pupil center and a point of surface reflection by the CAM-LED. In the interpolation, a point-of-gaze is obtained in a manner that a sample point is obtained from four calibration points, and the positional relationship between the pupil center in an input frame and the point of surface reflection by the CAM-LED is expressed as linear interpolation of the calibration points.

An experiment environment with the LED-AP is shown in FIGS. 8A-8D (lower right). The experiment was conducted in a general indoor light environment. The subject A sat at a position apart from the wall and gazed at 20 markers on the wall. The eyeball image obtaining means 102 was set slightly below the face of the subject A. The distance between the face and the eyeball image obtaining means 102 was set to be about 0.6 m. The environment light detecting device 112 was set behind the subject A so as to capture all the markers on the wall.

A Point Grey Dragonfly Express camera (640×480 pixels, B/W, 30 Hz) was used as the eyeball image obtaining means 102. As light sources of the LED-AP, nine Luxeon Rebel high-power LEDs (3 W, white) by Philips were used. Pattern light projected imaging shooting, and image obtainment were performed by a personal computer (Intel Core i7-960, 3.06 GHz, 8 GB, RAM). Image processing was performed in an environment of Matlab R2010b and Image Processing Toolkit on the same personal computer. In the experiment of the pattern illumination markers, the positional relationship between the subject A and the eyeball image obtaining means 102 and the configurations for image obtainment and of a processing tool were the same as above. However, four low-output (15 mA) infrared LEDs were used.

In order to evaluate errors in point-of-gaze estimation in environments different in depth, the experiment was conducted under two respective conditions where the distance between the subject A and the wall was set to be 1900 mm (first condition 1) and 3000 mm (second condition). The personal parameter of the subject A obtained under the first condition 1 was applied to estimation on the first condition 1 and estimation on the second condition. Further, calibration by interpolation was also conducted on the first condition likewise.

Figure 14:
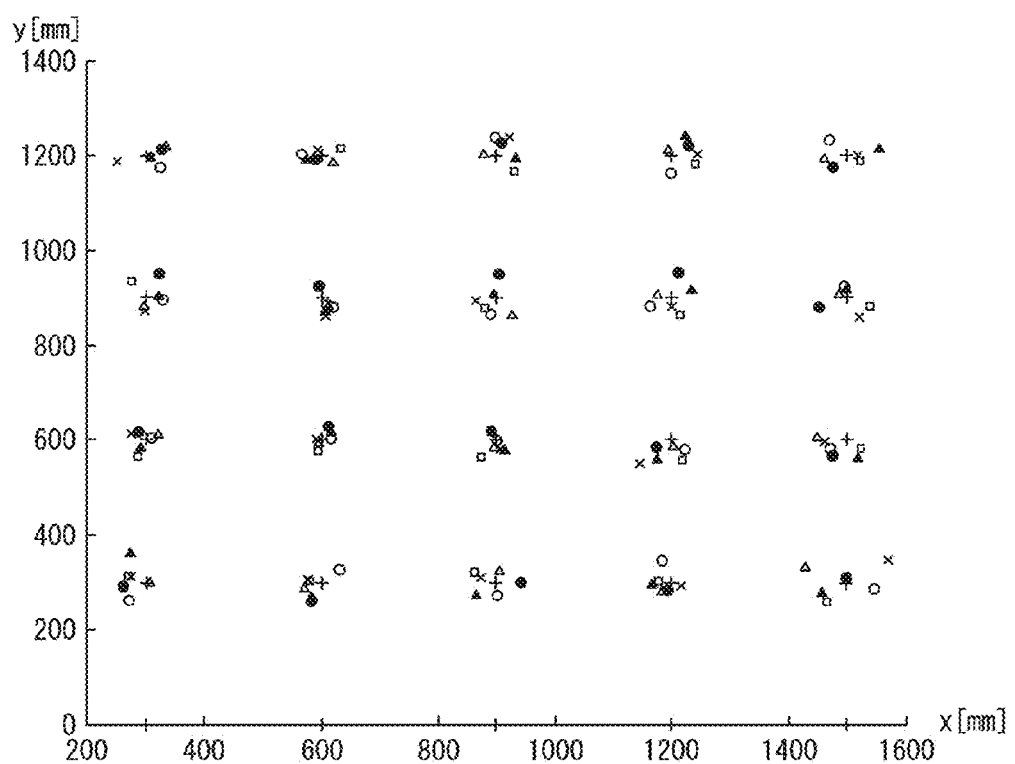
FIG. 14 is a graph representation showing results of point-of-gaze estimation on a first condition.
Figure 15:
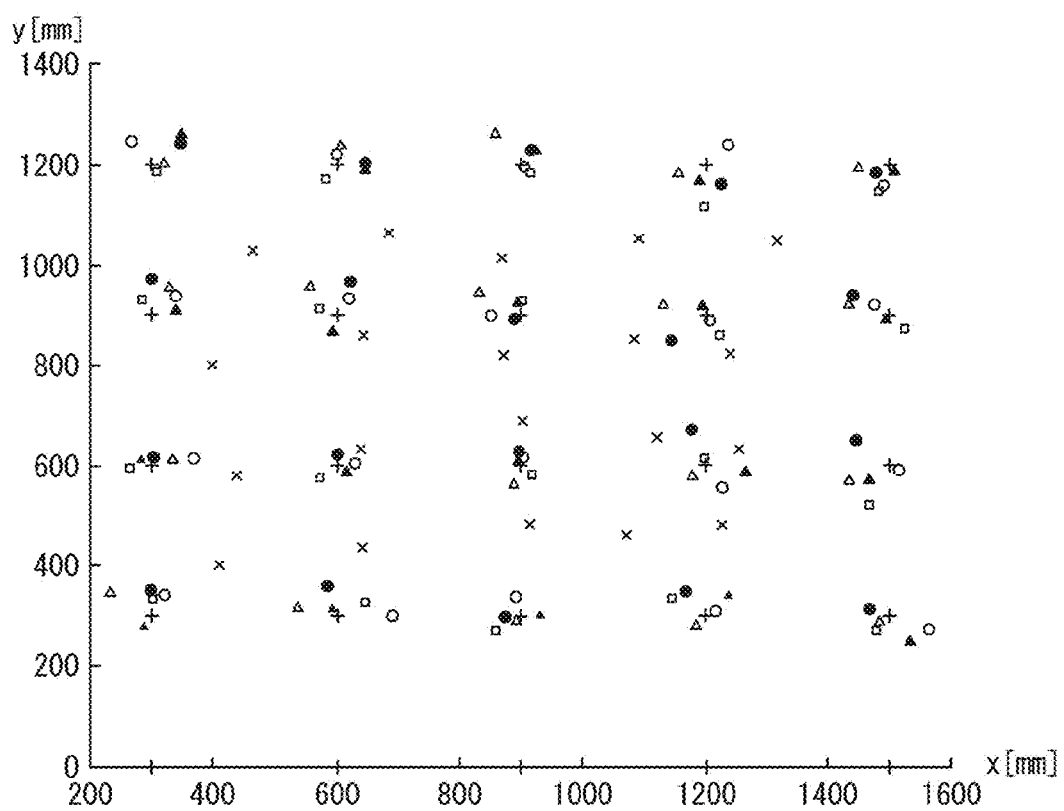
FIG. 15 is a graph representation showing results of point-of-gaze estimation on a second condition.

FIG. 13 indicates errors in the estimated angle of the point-of-gaze where the eye of each subject A is regarded as (x, y, z)=(900, 600, 1900) [mm] and (900, 600, 3000) [mm] (comparison between the conventional method (interpolation) and the method according to the present invention which introduces the personal parameter). The unit is degree (deg). Further, FIG. 14 shows results of the point-of-gaze estimation on the first condition. FIG. 15 shows results of the point-of-gaze estimation on the second condition. In FIGS. 14 and 15, a mark "+" represents a gaze target marker (Ground truth). Marks "○", "●", "△", "▲", and "□" represent respective results of estimation in different subjects obtained by the method according to the present invention. The number of the subjects is five (five user/subjects). The mark "x" represents a result of the user 1 (subject 1) by interpolation.

It is noted that the projected light of the LED-AP was projected at (1490, 1200), (895, 1200), (300, 1200), (1430, 750), (835, 750), (300, 750), (1450, 300), (820, 300), and (320, 300) [mm] in the coordinate system. Further, the eyeball was located at (900, 600, 1900) [mm] (first condition) and (900, 600, 3000) [mm] (second condition). In the example according to the present embodiment (method according to the present invention), it could be confirmed that estimation can be done within an error of one degree or smaller on both of the two conditions different in depth. In the interpolation, excellent results were obtained on the same condition (first condition) as a case where calibration is performed. However, it can be understood that the accuracy decreases on the condition in which the depth is different.

INDUSTRIAL APPLICABILITY

According to the present invention, the gaze direction of a customer in a store can be detected. This can realize product display with high economic efficiency. When it is boarded on a vending machine, sales optimization can be achieved. Further, movement of the gaze direction of the subject A in living space can be analyzed. Accordingly, a living environment friendly to the subject A can be designed. Moreover, ubiquitous/ambient interfaces using information on the gaze direction in living space can be developed as an example of application to user interfaces. For example, a driver's point-of-gaze can be monitored so that an alert can be issued, which can contribute to safe automobile driving and the like.

In particular, the gaze direction is important as information obtained from children and/or the elderly. Accordingly, a non-wearing type eye tracking interface can play a significant role. For example, information on the gaze direction is a key to diagnosis of children's developmental disability, such as autism, etc. Diagnosis on children can be made using information on the gaze direction obtained in an environment of an experimental laboratory. By implementing the point-of-gaze detection device, the point-of-gaze detecting method, the personal parameter calculating device, or the personal parameter calculating method according to the embodiment of the present invention, one can obtain highly accurate information on the gaze direction of infants in a non-wearing manner. Thus, significant contribution to the fields of life science and robots can be expected.

Furthermore, according to the present invention, peripheral vision of a subject can be estimated. That is, in the present invention, the reflection image of the subject's eyeball surface can be obtained. Accordingly, what angle from the subject's gaze center a subject can see an object in a peripheral view field can be determined on the basis of the surface reflection image. As a result, whether or not a subject can see an object in a peripheral view field can be determined. Also, in how wide a view region the subject can see the object can be measured. For example, information on the peripheral vision (e.g., in a situation in which a person jumps in front of an automobile) is important for automobile drivers. Information on the peripheral view can be measured accurately.

Yet further, in the conventional point-of-gaze detection, calibration is performed on, for example, the central position of the subject's pupil projected on an eye observation camera and the subject's point-of-gaze prior to point-of-gaze detection. Accordingly, if the eye observation camera is displaced from a fitting position after calibration, the subject's point-of-gaze cannot be estimated. According to the present invention, the eyeball pose is estimated from the image of the subject's eyeball. Then, the subject's point-of-gaze is estimated on the basis of the estimated eyeball pose. Thus, even if the eye observation camera is displaced from the fitting position before point-of-gaze detection, influence of such a displacement on the result of point-of-gaze detection can be reduced.

REFERENCE SIGN LIST

A subject
PoG point-of-gaze
GRP first reflection point
CRP second reflection point
cGRP corrected reflection point
100 point-of-gaze detection device
102 eyeball image obtaining means
104 reflection point estimating means
106 corrected reflection point calculating means
108 point-of-gaze detecting means
110 pose calculating means
112 environment light detecting device
200 personal parameter calculating device
206 reflection point detecting means
208 personal parameter calculating means

The invention claimed is:

1. A point-of-gaze detection device to detect a point-of-gaze of a subject toward a surrounding environment, comprising:
an eyeball image obtaining section configured to obtain an eyeball image of the subject;
a reflection point estimating section configured to estimate a first reflection point, at which incoming light in an optical axis direction of an eyeball of the subject is reflected, from the eyeball image;
a corrected reflection point calculating section configured to calculate a corrected reflection point as a corrected first reflection point by correcting the first reflection point on the basis of a personal parameter indicative of a difference between a gaze direction of the subject and the optical axis direction of the eyeball; and
a point-of-gaze detecting section configured to detect the point-of-gaze on the basis of light at the corrected reflection point and light in the surrounding environment.

2. The device of claim 1, further comprising:
a pose calculating section configured to calculate a pose of the eyeball from the eyeball image;
wherein the reflection point estimating section estimates the first reflection point on the basis of the pose of the eyeball and a geometric model of the eyeball.

3. The device of claim 1, wherein
the reflection point estimating section estimates the first reflection point on the basis of a model on the assumption that the gaze direction of the subject is parallel to the optical axis direction of the eyeball of the subject.

4. The device of claim 1, wherein
the light in the surrounding environment is light of an LED array projector.

5. The device of claim 1, wherein
the light in the surrounding environment is light of a pattern illumination marker.

6. A point-of-gaze detecting method for detecting a point-of-gaze of a subject toward a surrounding environment, comprising:
obtaining an eyeball image of the subject;
estimating a first reflection point, at which incoming light in an optical axis direction of an eyeball of the subject is reflected, from the eyeball image;
calculating a corrected reflection point as a corrected first reflection point by correcting the first reflection point on the basis of a personal parameter indicative of a difference between a gaze direction of the subject and the optical axis direction of the eyeball; and
detecting the point-of-gaze on the basis of light at the corrected reflection point and light in the surrounding environment.

7. A personal parameter calculating device to calculate a personal parameter indicative of a difference between a gaze direction of a subject and an optical axis direction of an eyeball of the subject, comprising:
an eyeball image obtaining section configured to obtain an eyeball image of the subject;
a reflection point estimating section configured to estimate a first reflection point, at which incoming light in the optical axis direction of the eyeball is reflected, from the eyeball image;
a reflection point detecting section configured to detect a second reflection point, at which light coming from a point-of-gaze of the subject is reflected, from the eyeball image; and
a personal parameter calculating section configured to calculate the personal parameter of the subject based on the first reflection point and the second reflection point.

8. The device of claim 7, further comprising:
a pose calculating section configured to calculate a pose of the eyeball from the eyeball image;
wherein the reflection point estimating section estimates the first reflection point on the basis of the pose of the eyeball and a geometric model of the eyeball.

9. The device of claim 7, wherein
the reflection point estimating section estimates the first reflection point on the basis of a model on the assumption that the gaze direction of the subject is parallel to the optical axis direction of the eyeball.

10. A personal parameter calculating method for calculating a personal parameter indicative of a difference between a gaze direction of a subject and an optical axis direction of an eyeball of the subject, comprising:
obtaining an eyeball image of the subject;
estimating a second reflection point, at which incoming light in an optical axis direction of the eyeball is reflected, from the eyeball image;
detecting a first reflection point, at which light coming from a point-of-gaze of the subject is reflected, from the eyeball image; and
calculating the personal parameter of the subject on the basis of the first reflection point and the second reflection point.

11. A non-transitory computer readable storage medium which stores a program to allow a computer to execute point-of-gaze detection for detection of a point-of-gaze of a subject toward a surrounding environment,
wherein the program includes:
obtaining an eyeball image of the subject;
estimating a first reflection point, at which incoming light in an optical axis direction of an eyeball of the subject is reflected, from the eyeball image;
calculating a corrected reflection point as a corrected first reflection point by correcting the first reflection point on the basis of a personal parameter indicative of a difference between a gaze direction of the subject and the optical axis direction of the eyeball; and
detecting the point-of-gaze on the basis of light at the corrected reflection point and light in the surrounding environment.

12. A non-transitory computer readable storage medium which stores a program to allow a computer to execute personal parameter calculation for calculation of a personal parameter indicative of a difference between a gaze direction of a subject and an optical axis direction of an eyeball of the subject,
wherein the program includes:
obtaining an eyeball image of the subject;
estimating a second reflection point, at which incoming light in the optical axis direction of the eyeball is reflected, from the eyeball image;
detecting a first reflection point, at which light coming from a point-of-gaze of the subject is reflected, from the eyeball image; and
calculating the personal parameter of the subject on the basis of the first reflection point and the second reflection point.

* * * * *